(12) United States Patent
Verheul-Koot et al.

(10) Patent No.: US 8,163,303 B2
(45) Date of Patent: *Apr. 24, 2012

(54) NUTRITIONAL COMPOSITION FOR THE TREATMENT OF PRESSURE ULCERS

(75) Inventors: Maria Anna Verheul-Koot, Zegveld (NL); Chantal Nelleke Kleijer, Delft (NL); Robert Johan Joseph Hageman, Waddinxveen (NL); Roelof Andre Bork, Zoetermeer (NL); Maud Goethals, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 493 days.

This patent is subject to a terminal disclaimer.

(21) Appl. No.: 11/861,323

(22) Filed: Sep. 26, 2007

(65) Prior Publication Data

US 2008/0020062 A1 Jan. 24, 2008

Related U.S. Application Data

(62) Division of application No. 10/993,348, filed on Nov. 22, 2004, which is a division of application No. 09/462,678, filed as application No. PCT/NL99/00295 on May 12, 1999, now Pat. No. 6,846,494.

(30) Foreign Application Priority Data

May 12, 1998 (EP) ..................................... 98201576

(51) Int. Cl.
*A61K 8/00* (2006.01)
*A61K 38/00* (2006.01)

(52) U.S. Cl. ............... 424/439; 514/2; 514/23; 514/251
(58) Field of Classification Search .................. None
See application file for complete search history.

(56) References Cited

U.S. PATENT DOCUMENTS

| | | |
|---|---|---|
| 5,053,387 A | 10/1991 | Alexander |
| 5,656,588 A | 8/1997 | Zaloga et al. |
| 5,968,896 A | 10/1999 | Bell et al. |
| 6,139,872 A | 10/2000 | Walsh |
| 6,203,818 B1 | 3/2001 | Vester |
| 6,846,494 B1 | 1/2005 | Verheul-Koot et al. |

FOREIGN PATENT DOCUMENTS

| | | | |
|---|---|---|---|
| EP | 367724 | | 5/1990 |
| GB | 2274235 A | * | 7/1994 |
| WO | 93/16595 | | 9/1993 |

OTHER PUBLICATIONS

Jaren-Galan et al . Paprika (Capsicum annuum) oleoresin extraction with supercritical carbon dioxide. J. Food. Agri, 1999, vol. 47, p. 3558-3564.*

* cited by examiner

*Primary Examiner* — Lakshmi Channavajjala
(74) *Attorney, Agent, or Firm* — Young & Thompson

(57) ABSTRACT

The invention pertains to a method of treating or preventing pressure ulcers, comprising enterally administering to a subject in need thereof a composition comprising proteins, carbohydrates, fats, arginine or equivalents thereof, ascorbic acid equivalents and a-tocopherol equivalents, wherein arginine or equivalents thereof is administered in a daily amount of 3-15 g, ascorbic acid equivalents are administered in a daily amount of 180-840 mg and a-tocopherol equivalents are administered in a daily amount of 50-400 mg.

12 Claims, No Drawings

NUTRITIONAL COMPOSITION FOR THE TREATMENT OF PRESSURE ULCERS

CROSS REFERENCE TO RELATED APPLICATIONS

This application is a division of co-pending application Ser. No. 10/993,348 filed on Nov. 22, 2004, which is a division of co-pending application Ser. No. 09/462,678, filed on May 5, 2000. Application Ser. No. 09/462,678 is the national phase of PCT International Application No. PCT/NL99/00295 filed on May 12, 1999 under 35 U.S.C. §371. The entire contents of each of the above-identified applications are hereby incorporated by reference.

The invention relates to a nutritional composition suitable for the treatment and prevention of pressure ulcers.

BACKGROUND

Pressure ulcers (decubitus) occur relatively often, especially in surgery patients and immobile persons, such as part of the elderly, that have to stay in bed for extended periods. Some parts of the body, e.g. elbows, heels, hips, coccyx, sacrum, scapulae, are affected by the pressure forces exerted by the weight of the body. The severity of pressure ulcers is classified in various stages. In the first stage, pressure and shearing forces cause pinching of the subcutaneous tissue, occlusion of the capillaries and lymphatics and poor vascularisation in deep tissue layers. Prolonged pressure initiates tissue damage at the skin surface. This results in decreased cell production in the epidermis and thinning of the skin. Blood vessels in the skin are impaired and cause redness. In the second stage, the basal membrane becomes detached from the epidermis. Oedema and blisters occur. In the third stage, the epidermis becomes more and more impaired and the skin surface is also affected. In the further stages, necrosis of deep tissue layers becomes visible on the skin surface. The nutritional condition of decubitus patients is often poor, as a result of insufficient nutrition following surgical operations, malnourishment, loss of components from wounds, immobility, physical disability or other impediments.

Prevention and curing of pressure ulcers first of all requires ameliorating extrinsic factors around the wound area, such as reducing the pressure, friction and shear forces, moisture and temperature.

A method of stimulating wound healing by administering zinc, vitamins A and C, selenium, β-carotene and thiamine is disclosed in EP-A-564804. A liquid composition containing 62.5 g/l (25 energy %) of proteins, 34 g/l (30 en. %) of fats and 113 g/l (45 en. %) of carbohydrates may be used. Other vitamins and trace elements may also be present. Pressure ulcers are mentioned among the conditions that would require such enhanced wound healing.

EP-A-367724 discloses immunostimulatory compositions containing, per unit dose (in 1.5 l), 3-40 g (18.75 g) of arginine, 0.1-4 g (1.9 g) of RNA, 0.1-20 g (3 g) of ω-3 polyunsaturated fatty acids (pufa's) comprising 1-2 g of EPA and 0.25-1 g of DHA, and 0.1-20 g (3.6 g) of ω-6 pufa's (linoleic acid). The compositions contain 22 en. % of proteins, 28 en. % of fats and 53 en. % of carbohydrates. Pressure ulcers are not mentioned as conditions for which the immunostimulatory compositions might be useful.

U.S. Pat. No. 5,053,387 discloses a composition for treating traumatic injury, containing arginine (1-3 en. %), intact protein (20-30 en. %), fats (7-15 en. %, containing EPA and linoleic acid with an ω-6/ω-3 ratio of about 1.5) and carbohydrates (65-70 en. %), and further zinc, vitamin A and vitamin C.

A liquid nutritional composition containing arginine for trauma and surgery patients, not including pressure ulcer patients, is disclosed in WO 93/16595. The composition contains 20 en. % of proteins, 24 en. % of fats and 56 en. % of carbohydrates. Arginine accounts for 1-3 en. % of the energy. The ratio of linoleic to a-linolenic acid is between 3.5 and 5.5. The caloric density is 1.2-1.5 kcal/ml and the calorie to nitrogen ratio is between 112 ad 145. The composition further contains vitamins and trace elements in 1 to 2 times the recommended daily amounts.

WO 96/08966 discloses a method of enhancement of wound healing by nitrogen monoxide (NO), which comprises the administration of NO-enhancing compounds such as nitrosylated amines, antioxidants such as vitamins C and E, and other components such as analgesics. Neither pressure ulcers nor nutritional compositions are contemplated in this document.

DESCRIPTION OF THE INVENTION

It was found now that a composition which is effective against pressure ulcers should contain a combination of nutrients which does not only improve wound healing, but also has an effect in the preceding stages of improving blood circulation and controlling inflammation. Such an effective composition, when in liquid form, should contain arginine (3-15 g/l, preferably 5-10 g/l), vitamin C (3-14 times the recommended daily level, RDA), vitamin E (5-40 times the RDA) and preferably also zinc at a rate of at least 8 mg per l or per day, with an adequate zinc/copper ratio. A further improved composition also contains increased levels of carotenoids, minerals (Na, K, Cl) and/or flavonoids (8-40 mg/l).

The arginine to be used in the composition according to the invention may be in form of the free amino acid, or in the form of arginine-rich peptides or proteins such as pea proteins, or as metabolic equivalents of arginine such as ornithine or citrulline. The amount of arginine to be used is 3-15 g/day, preferably 5-10 g/day.

The level of vitamin C is expressed herein as ascorbic acid equivalents, which comprise vitamin C (ascorbic acid) and compounds that can be transformed to ascorbic acid in the body, such as dehydroascorbic acid, ascorbyl palmitate and other ascorbyl esters. The amount of ascorbic acid equivalents is from 180 mg or 200 up to 840 mg or more per day. The preferred range is 300-780, especially 350-700 mg/day.

The level of vitamin E is expressed herein as tocopherol equivalents, which comprise a-tocopherol and equivalents. Thus, 1 mg of a-tocopherol equivalent (TE) (=1.5 IU of vitamin E) corresponds to 1 mg of D-a-tocopherol, 2.0 mg of D-β-tocopherol, 10 mg of D-γ-tocopherol, 30 mg of D-d-tocopherol, 2 mg of D-a-tocotrienol or 18.6 mg of D-β-tocotrienol. The amount of tocopherol equivalent to be used is 50-400 mg/day. Preferably, the minimum level is 100, more preferably 120, especially 180 mg/day, and the preferred upper limit is 320, more preferably 250 mg/day.

The efficacy of the combination described above is further increased by the presence of flavonoids, e.g. at a level of 8-40, in particular 10-30 mg/day. According to the invention, flavonoids are understood to comprise hydroxy-substituted compounds having the flavone skeleton (2-phenyl-chromone=2-phenyl-benzopyrone) and isomers thereof such as the isoflavones (3-phenyl-chromones), chalcones (2-cinnamoyl-phenols) and aurones (2-benzylidene-benzofuranones). Also the anthocyanidins (which differ from the flavones by the presence of a pyrylium moiety instead of the pyrone moiety) are considered to be included in the flavonoids. The hydroxy functions of the flavonoid compounds may be, and preferably are, partly alkylated or glycosylated, as is the case in natural compounds, such as anthocyans (=glycosylated anthocyanidins) and glycosylated flavonols. Among the flavones, the flavonols, especially the flavonotetraols and higher hydroxylated analogues, such as kaempferol, quercitin and myrecitin, and the methylated analogues such as sinensetin, tangeretin and nobiletin, as well as the glycosides such as rutin and myricitrin, are preferred. Among the isoflavones, daidzein and genistein are examples of preferred compounds, and among the anthocyanidins, peonidin, cyanidin, pelargonidin, delphinidin, petunidin and valvidin are preferred. Flavanones (=2,3-dihydroflavones) such as hesperetin and naringin are other preferred flavonoids. The use of a mixture of flavonoids, such as in natural plant extracts or mixtures of plant (e.g. citrus, tea, grape) extracts, is advantageous. Preferably, the flavonoids according to the invention comprise at least 40% of flavonols and at least 10% of anthocyans, more preferably at least 60% and at least 15%, respectively. Analogues such as catechins, proanthocyanidins and other tannins, are preferably not present, i.e. account for less than 3% of the flavonoids.

The composition of the invention is aimed at improving blood circulation, accelerated curing and improving the immune status, and at compensating for loss of nutritional components that occurs during disease. Also, it stabilises cell membranes against radical attack. In addition to the tocopherols and ascorbate, this function is enhanced by glutathione and NADPH, which are made available through administration of methionine, cofactors and energy (carbohydrates).

Further preferred components are vitamins B6 (pyridoxal), B12 (cyanocobalamine) and folic acid, each being present at about 3 times the recommended average daily administration level (such as the RDA). Vitamins B1 (thiamin) and B2 (riboflavin), copper, zinc and manganese, are each preferably present at twice the RDA. The zinc to copper ratio should preferably be in the range of 7-14, especially 8-11. Iron, cobalt, iodide, chromium, selenium, fluoride, molybdenum and pantothenic acid, vitamin A (in retinol equivalents, RE), vitamin D, vitamin K, niacin (in niacin equivalents, NE), biotin and inositol, are preferably present at 0.5-4, especially 1-2 times the RDA values for each. Minerals should preferably be present as follows (amounts per day): sodium 200-1200 mg, chloride 240-1400 mg, potassium 500-1800 mg, calcium 500-1000 mg, phosphorus 400-900 mg and magnesium 150-400 mg.

Carotenoids (which, for the purpose of the invention, include xanthins and xanthophylls) are preferably present at a level of 0.8-16 mg, preferably 1-6 mg per day. The carotenoids are advantageously in their natural form, as can be found in extracts from plants like tomato, pepper, marigold and fruit of oil palm. Preferably, such extracts are mixed and the composition may e.g. contain lutein (20-60%), lycopene (1-30%), a-carotene (5-25%), β-carotene (5-40%), cryptoxanthine (1-15%) and zeaxanthine (1-15%).

Choline or a metabolic equivalent thereof such as betaine or phosphatidyl choline, is preferably present at a level of 20-3000 mg/day, which may comprise e.g. 1 g or more of phosphatidyl choline. Carnitine, creatine and taurine may be present at levels of 10-100 mg, 100-1000 mg and 10-100 mg, respectively, per day.

Long-chain PUFA's of the ω-3 series, especially EPA and DHA, can also advantageously be present. The total of EPA and DHA is advantageously between 0.1 an 1.0 g/day. The ω-6/ω-3 ratio of the LC-PUFA's is between 1 and 6, preferably between 2 and 5. Linoleic acid (ω-6) may also be present, preferably at a level of at least 0.1 g/day.

Another advantageous group of components of the composition of the invention are dietary fibres, which can include soluble non-starch polysaccharides such as gum arabic or pectin, insoluble non-starch polysaccharides such as cellulose, hemicellulose and lignin, oligosaccharides such as inulin or galacto-oligosaccharides and/or resistant starch. The preferred level of dietary fibre is 3-20 g/day or 3-20 g/liter.

Carbohydrates, flavourings and yeast extracts may further improve the nutritive and organoleptic quality of the composition. The product is preferably packed in a form which protects it from oxygen and light, especially UV, e.g. in 100-1000 ml units. The smaller amounts are useful as food supplements, whereas the larger amounts are suitable as complete foods, for enteral use.

The amounts of the important components arginine, vitamin C and vitamin E can also be defined with reference to a unit energy content (1000 kcal) or to a unit volume (1 liter), as in the appending claims. A similar definition can be given for preferred components such as flavonoids (16-60 mg/1000 kcal, 16-80 mg/l), carotenoids (1.6-20 mg/1000 kcal, 1.6-24 mg/l), zinc (18-60 mg/1000 kcal, 18-75 mg/l) and copper (2.5-10 mg/1000 kcal, 2.5-12 mg/l).

By way of summary, table 1 shows art-recommended and preferred ranges for compositions, as well as examples of formulations that can be used as a liquid composition which provides the total daily minimum nutritional supply, and may be supplemented with energy as required.

TABLE 1

| nutrient | unity | rec. daily amt.* | range (per day) | preferred range (per day) | example II drink booster (400 ml/d) | example I tube booster (1 l/day) |
|---|---|---|---|---|---|---|
| energy | kcal | | | 300-1300 | 500 | 1000 |
| protein | g | | | 25-90 | 40 | 64 |
| carbohydrate | g | | | 40-160 | 56 | 126 |
| fat | g | | | 5-36 | 14 | 27 |
| arginine | g | | 3-15 | 5-10 | 6 | 7 |
| methionine | g | | 0.8-5 | 1-3 | 0.9 | 1.8 |
| ascorbic acid | mg | 50-60 | 180-840 | 300-700 | 500 | 530 |
| tocopherol (TE) | mg | 8-10 | 50-400 | 80-250 | 200 | 200 |
| flavonoids | mg | | 8-40 | 10-30 | 23 | 23 |
| vitamin A (RE) | μg | 800-1000 | 200-1500 | 400-1200 | 500 | 900 |
| thiamin (B1) | mg | 1.1-1.5 | 1-9 | 2-5 | 3.0 | 3.6 |
| riboflavin (B2) | mg | 1.3-1.8 | 1-10 | 1.7-5 | 3.0 | 3.7 |
| vitamin B6 | mg | 1.4-2 | 4-25 | 5-10 | 6.0 | 6.8 |
| vitamin B12 | μg | 2 | 2-100 | 2.5-20 | 3.0 | 4.2 |

TABLE 1-continued

| nutrient | unity | rec. daily amt.* | range (per day) | preferred range (per day) | example II drink booster (400 ml/d) | example I tube booster (1 l/day) |
|---|---|---|---|---|---|---|
| vitamin D | μg | 5-10 | 1-40 | 8-20 | 10 | 13 |
| folic acid | μg | 150-200 | 300-2000 | 400-1200 | 600 | 680 |
| pantothenic acid | mg | 4-7 | 4-40 | 6-24 | 8 | 10 |
| biotin | μg | 30-100 | 40-800 | 50-500 | 76 | 136 |
| vitamin K1 | μg | 45-80 | 20-240 | 50-120 | 56 | 60 |
| niacin (NE) | mg | 12-20 | 6-80 | 35-75 | 51 | 64 |
| carnitine | mg |  | 10-100 | 10-40 | 15 | 15 |
| inositol | mg |  | 10-250 | 20-250 | 50 | 50 |
| taurine | mg |  | 4-100 | 8-40 | 15 | 15 |
| choline (eq.) | mg |  | 20-3000 | 80-1000 | 100 | 1000 |
| carotenoids | mg |  | 0.8-16 | 1-8 | 4 | 4 |
| magnesium | mg | 270-400 | 80-600 | 150-400 | 160 | 360 |
| zinc | mg | 12-15 | 8-80 | 14-45 | 22 | 36 |
| iron | mg | 10-15 | 5-60 | 5-20 | 8 | 14 |
| copper | mg | 1-3 | 1-12 | 2-10 | 3.0 | 3.9 |
| cobalt | μg |  | 0-10 | 1-6 | 3 | 3 |
| manganese | mg | 2-5 | 1-30 | 2-20 | 8.0 | 9.8 |
| iodine | μg | 150 | 25-500 | 50-250 | 100 | 160 |
| selenium | μg | 40-70 | 35-300 | 50-250 | 100 | 126 |
| chromium | μg | 50-200 | 10-100 | 15-75 | 33 | 54 |
| molybdenum | μg | 75-250 | 35-300 | 40-200 | 80 | 160 |
| fluoride | mg | 1.5-4 | 0.5-16 | 0.5-2.5 | 0.6 | 2.0 |
| chloride | mg |  | 180-2000 | 240-1500 | 350 | 1300 |
| sodium | mg |  | 120-2400 | 200-1200 | 250 | 1000 |
| potassium | mg |  | 200-2000 | 500-1800 | 800 | 1500 |
| calcium | mg | 800-1200 | 300-1500 | 500-1000 | 820 | 650 |
| phosphorus | mg | 800-1200 | 200-1400 | 400-900 | 720 | 500 |

*standard recommended daily amount, such as RDA

Example I

The ingredients as listed in table 1 in 1000 times the amounts given in the last column of table 1 were mixed in a tank, homogenised using methods known in the art, and brought to a total volume of 1000 l. The mixture was packed in 500 mls flask for use as tube feeding.

Example II

The ingredients as listed in table 1 in 1000 times the amounts given in the 6th column of table 1 were mixed in a tank, homogenised using methods known in the art, and brought to a total volume of 400 l. The mixture was packed in 200 ml cartons.

Example III

The following ingredients: sodium 600 g, chloride 900 g, tocopherols 150 g, choline 800 g, no flavonoids and no carotenoids, and the further components at 1000 times the amount of column 6 of the table were mixed and packed as in example II. The product is a whitish drink and is especially suitable for the treatment of decubitus after substantial mineral loss, as in cases of chronic open wounds.

The invention claimed is:

1. A nutritional composition suitable for the treatment of pressure ulcers, comprising proteins, carbohydrates, fats, arginine or equivalents thereof, ascorbic acid equivalents and a-tocopherol equivalents and, wherein the composition comprises, in a daily unit dose, 3-15 g of arginine or equivalents thereof, zinc in a daily unit dose of 8-80 mg, copper in a daily unit dose of 2-10 mg, α-tocopherol equivalents in a daily unit dose of 50-400 mg, and 0.8-16 mg of carotenoids comprising xanthophylls.

2. The nutritional composition of claim 1, wherein said xanthophylls are selected from lutein, cryptoxanthin and zeaxanthin.

3. The nutritional composition of claim 2, wherein said carotenoids comprise 20-60 wt. % lutein.

4. The nutritional composition of claim 2, wherein said carotenoids comprise 1-15 wt. % cryptoxanthin.

5. The nutritional composition of claim 2, wherein said carotenoids comprise 1-15 wt. % zeaxanthin.

6. The nutritional composition of claim 1, wherein said carotenoids further comprise 1-30 wt. % lycopene.

7. The nutritional composition of claim 1, wherein the carotenoids comprise 20-60% lutein, 1-30% lycopene, 5-25% a-carotene, 5-40% β-carotene, 1-15% cryptoxanthin and 1-15% zeaxanthin.

8. The nutritional composition of claim 1, wherein the composition comprises, in a daily unit dose, 180-840 mg of ascorbic acid equivalents.

9. The nutritional composition according to claim 1, wherein said xanthophylls comprise 1-20% lutein, 1-15% cryptoxanthin, and/or 1-15% zeaxanthin.

10. A nutritional composition suitable for treating pressure ulcers, said composition comprising zinc in a daily unit dose of 8-80 mg; copper in a daily unit dose of 2-10 mg; and carotenoids in a daily unit dose of 0.8-16 mg, wherein said carotenoids comprise 20-60% lutein, 1-30% lycopene, 5-25% a-carotene, 5-40% β-carotene, 1-15% cryptoxanthin and 1-15% zeaxanthin.

11. The nutritional composition of claim 10, wherein the composition comprises, in a daily unit dose, 180-840 mg of ascorbic acid equivalents.

12. The nutritional composition of claim 10, wherein the composition comprises, in a daily unit dose, 50-400 mg of α-tocopherol equivalents.

* * * * *